(12) United States Patent
Voland et al.

(10) Patent No.: US 9,042,510 B2
(45) Date of Patent: May 26, 2015

(54) IMAGE PROCESSING DEVICE OF A COMPUTER TOMOGRAPHY SYSTEM

(71) Applicant: Fraunhofer-Gesellschaft zur Foerderung der angewandten Forschung e.V., Munich (DE)

(72) Inventors: Virginia Voland, Fuerth (DE); Stefan Reisinger, Fuerth (DE); Michael Schmitt, Grossenseebach (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 164 days.

(21) Appl. No.: 13/779,322

(22) Filed: Feb. 27, 2013

(65) Prior Publication Data

US 2013/0235970 A1 Sep. 12, 2013

(30) Foreign Application Priority Data

Feb. 29, 2012 (DE) .......................... 10 2012 203 086

(51) Int. Cl.
*G06T 11/00* (2006.01)
*A61B 6/03* (2006.01)
*A61B 6/00* (2006.01)
*G01N 23/04* (2006.01)

(52) U.S. Cl.
CPC .............. *G06T 11/003* (2013.01); *A61B 6/032* (2013.01); *A61B 6/5205* (2013.01); *A61B 6/582* (2013.01); *G01N 23/046* (2013.01)

(58) Field of Classification Search
CPC ...... G06T 11/03; A61B 6/032; A61B 6/5205; A61B 6/582; G01N 23/046

USPC ........................... 378/4, 19, 20, 207; 382/131
See application file for complete search history.

(56) References Cited

U.S. PATENT DOCUMENTS 6,325,539 B1 12/2001 Bromberg et al.
6,912,265 B2 * 6/2005 Hebecker et al. ................. 378/4

(Continued)

FOREIGN PATENT DOCUMENTS

EP 2201895 6/2010

OTHER PUBLICATIONS

Patel, V. et al., "Self-calibration of a cone-beam micro-CT system".

(Continued)

*Primary Examiner* — Irakli Kiknadze
(74) *Attorney, Agent, or Firm* — Michael A. Glenn; Perkins Coie LLP (57) ABSTRACT

An image processing device of a computer tomography system includes an interface and a calibration data determiner. The interface is implemented to receive a first set of X-ray recordings of an object to be examined from first discrete recording angles and to receive a second set of X-ray recordings of the object to be examined from second discrete recording angles. The calibration data determiner is implemented to determine calibration data for the computer tomography system on the basis of the first set. The first set is further recorded during a first rotation run wherein the computer tomography system and the object to be examined rotate relative to each other, wherein the second set is recorded during at least a further rotation run after the first rotation run. On the basis of the calibration data and the first and second sets a computer tomography recording is reconstructable.

25 Claims, 6 Drawing Sheets

(56) References Cited

U.S. PATENT DOCUMENTS

| | | |
|---|---|---|
| 7,826,587 B1 | 11/2010 | Langan et al. |
| 7,844,027 B2 * | 11/2010 | Harding et al. .................. 378/9 |
| 2005/0232389 A1 | 10/2005 | Klingenbeck-Regn |
| 2007/0274456 A1 | 11/2007 | Holt |
| 2009/0028288 A1 | 1/2009 | Horiuchi et al. |
| 2009/0046916 A1 | 2/2009 | Matsuura |

OTHER PUBLICATIONS

Zeng, G.L. et al., "Backprojection-based imaging geometric parameter estimation".

* cited by examiner

IMAGE PROCESSING DEVICE OF A COMPUTER TOMOGRAPHY SYSTEM

CROSS-REFERENCE TO RELATED APPLICATIONS

This application claims priority from German Patent Application No. 102012203086.7, which was filed on Feb. 29, 2012, and is incorporated herein in its entirety by reference.

BACKGROUND OF THE INVENTION

Embodiments of the present invention relate to an image processing device of a computer tomography system, to a computer tomography system and to a method for determining calibration data for a computer tomography system.

In contrast to standard x-ray systems, computer tomography systems (CTs) offer the advantage that cross-section images may be computed both two-dimensionally and also three-dimensionally by means of a computer. This calculation is based on a plurality of digitized x-ray recordings which represent an object from different radiation angles and may be combined taking geometrical parameters of the CT into account. By means of an exact knowledge of such geometrical parameters or generally of the recording geometry, both in two-dimensional and also in three-dimensional computer tomography an artifact-free reconstruction of the sectional recordings may be realized.

Figure 3A:
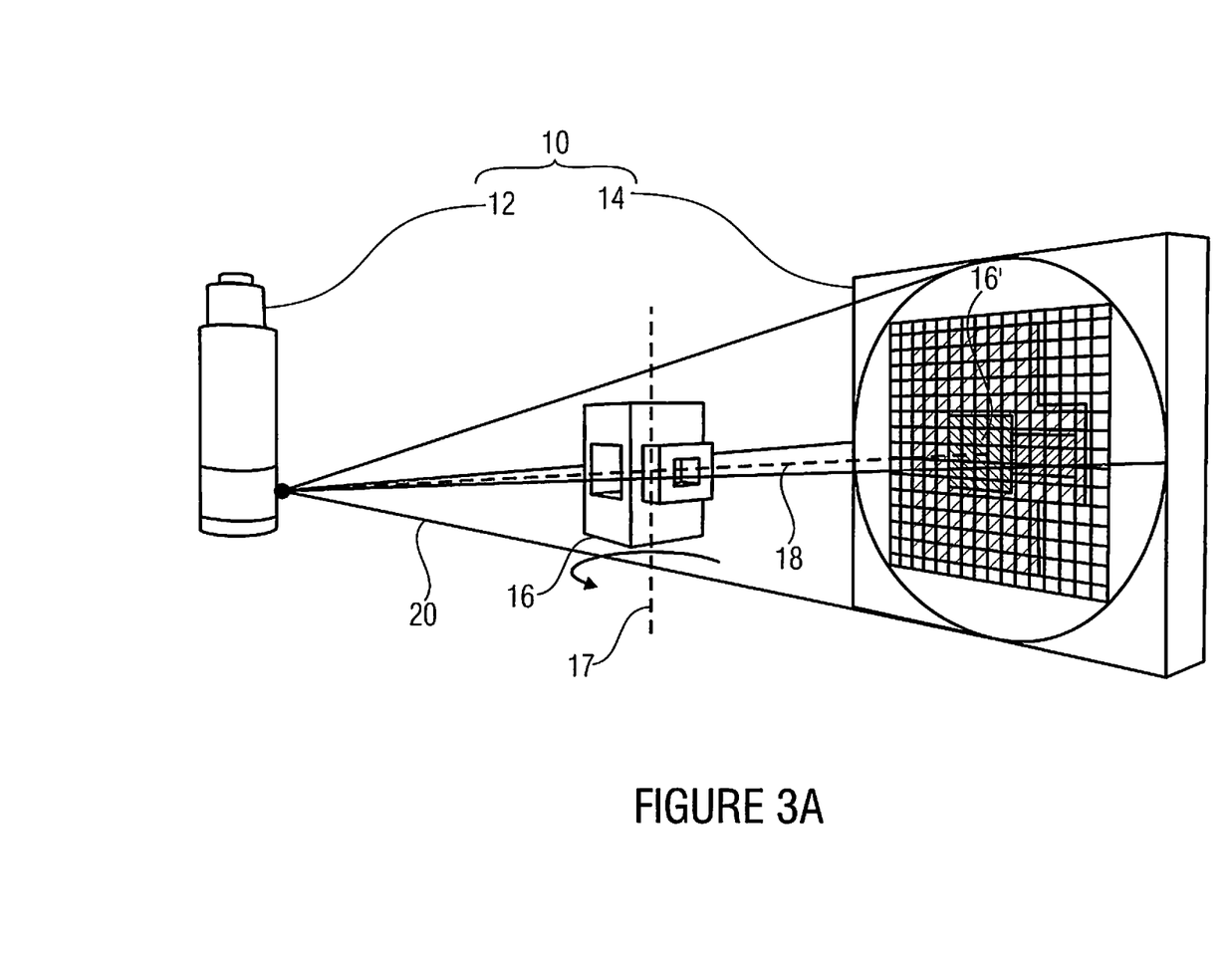
FIG. 3a-3b are schematical illustrations of computer tomography systems.
Figure 3B:
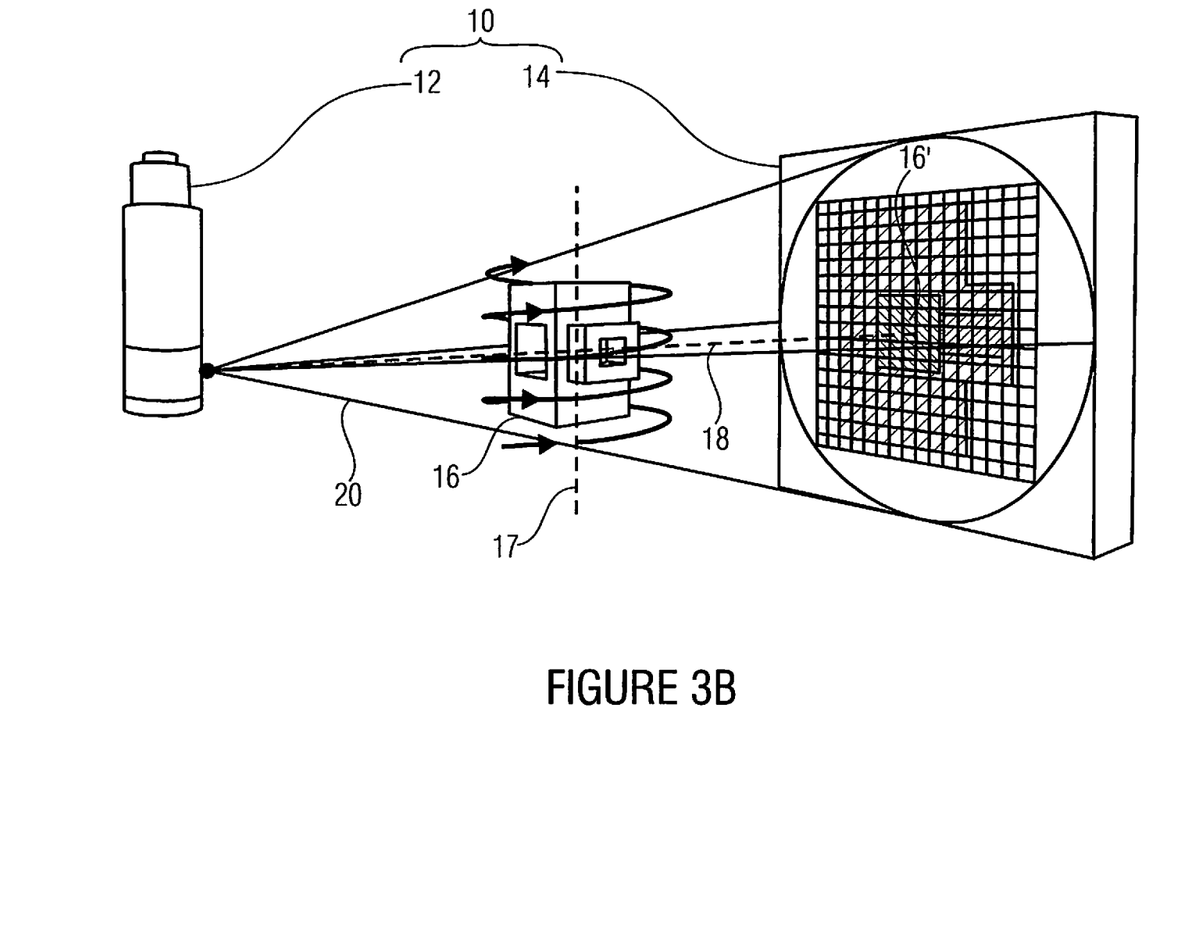

FIG. 3a shows a schematical setup of a computer tomography system in a cone beam geometry, while FIG. 3b shows a spiral computer tomography system which is also based on cone beam geometry.

The computer tomography system illustrated in FIG. 3a comprises a recording unit 10 having a radiation source 12, like e.g. an x-ray tube, and a radiation detector 14 associated with the radiation source. Between the radiation source 12 and the detector 14, the object 16 to be x-rayed is rotatably arranged. The object 16 may be rotated for example by means of a manipulation means around a rotary center or an axis of rotation 17. The axis of rotation 17 is approximately perpendicular (or possibly slightly tilted) with respect to an x-ray direction 18, which extends from the radiation source 12 to the radiation detector 14. This x-ray direction 18 is centered within the radiation cone 20 and passes in parallel to the central beam which is defined as a beam between the point of x-ray generation, i.e. a focal spot of the radiation source 12, and the center of the detector 14.

Radiation spreads along this beam cone, e.g. x-radiation of the radiation source 12, and x-rays the object 16. The absorption of the radiation by the object 16 may be detected by means of the radiation detector 14 in the form of an x-ray recording 16'. Here, the detector 14 transforms the received radiation of the radiation source 12 which is weakened by the object 16 into grey values which represent a measure for weakening. During the rotation a plurality of x-ray recordings 16' (projection) is recorded from different recording angles on the basis of which a computer tomography recording may be reconstructed.

This functioning may also be transferred to spiral or helix computer tomography systems as it is illustrated in FIG. 3b. A spiral computer tomography system basically comprises the same setup as the computer tomography system of FIG. 3a, wherein, however, the object 16 to be examined may for example be moved by means of the manipulation means itself or an additional lifting means, translationally along the axis of rotation 17, in addition to rotation. With respect to the setup illustrated in FIG. 3b it is possible due to the additional degree of freedom or the translational movement along the axis of rotation 17 to record different tomography or layer recordings of the object 16 from different recording angles in different horizontal planes. Thus, the rotary movement around the axis of rotation 17 is overlaid with the translational movement along the axis of rotation 17, so that the object 16 is rotated several times around the axis of rotation 17 (in connection with a vertical feed) and may thus be x-rayed spirally. The acquired spatial resolution and image sharpness depends on the geometric characteristics of the imaging system.

Using a plurality of x-ray recordings of the x-rayed object 16' from different recording angles and possibly in several layers or planes, a computer tomography recording is reconstructable, wherein the reconstruction is based on an exact knowledge of the geometrical parameters, like e.g. the relative position of the axis of rotation 17 with respect to the radiation source 12 or a possible tilting (e.g. in a range from 0° to 90°) of the axis of rotation 17. For a sufficient image quality in reconstruction it is assumed that the position of the axis of rotation 17 is known with an accuracy of $\pm 0.2 \times d_{\text{eff}}$ wherein $d_{\text{eff}}$ is the effective pixel size in the image. The effective pixel size $d_{\text{eff}}$ is the quotient of the distance of the detector elements $d_{Det}$ with respect to each other and the magnification factor M in the image: $d_{\text{eff}} = d_{Det}/M$.

If the relative position (i.e. not necessarily the absolute position) of the axis of rotation 17 is not sufficiently known, this has a negative effect in reconstruction onto the image quality. The image quality further depends on the position of the focal spot, wherein the same typically changes with varying x-ray parameters, like e.g. an x-ray voltage. The position of the rotary axis 17 is thus advantageously determined again for each computer tomography recording (data acquisition), but at least with changed operation parameters. In industrially used computer tomography—in contrast to medical computer tomography which basically deals with an unchanging task—there is also the fact that requirements, for example with respect to material to be examined or with respect to image quality, frequently vary. Consequently, system geometry and the associated geometrical parameters frequently change, so that for example a renewed determination of the position of the axis of rotation 17 or the rotation center is needed.

As it is described in patent document DE 4325351 C2, in known methods for determining the center of rotation a reference object is used. Here, for example a longitudinal object, like e.g. a rod, a needle or a wire is moved to different positions as a reference object by means of a manipulation unit and the positional data of the reference object are recorded. On the basis of the positional data geometrical parameters, like e.g. the relative position of the axis of rotation 17 with respect to the central beam (see x-ray direction 18) and the magnification factor M may be determined. Further, apart from the axis of rotation 17 the translational axis in the overall system may be determined when the reference object is moved in translation. In addition, the method offers the possibility to output a quality factor which forms a measure for the reliability of the calculation of the center of rotation. An alternative method for which for example a translational object movement in the central plane is needed determines the geometrical data by means of imaging a spherical reference object which is moved via a lift axis.

After a successful determination of the axis of rotation 17 or the rotary center, the projection data set of any object to be recorded which is recorded at the same axis position and using the same x-ray parameters may be reconstructed artifact-free. This applies in particular to CTs based on fan-beam geometry or cone beam geometry. However, with the above described methods, the error sources explained in the following may not be ruled out completely which may possibly lead to a decrease of precision in imaging.

Errors for example result by the reference object being exchanged by the object to be imaged 16 before the actual recording but after calibration. By this, the measurement environment, like e.g. ambient temperature, is changed by the exchange. Further, the rotary center 17 may be shifted by the exchange of the object 16 wherein here given a corresponding magnification already a shifting by several micrometers is sufficient to affect image quality. One possibility to minimize this is to attach the reference object for example above the object to be examined. After determining the axis of rotation 17 the reference object may for example be removed via a lift axis from the image area or the reconstruction area may be restricted vertically to the object 16 to be examined.

As an alternative to the above-described method it is also possible to determine geometrical parameters like e.g. the axis of rotation 17 or the center of rotation by means of a pre-scan before data acquisition for the computer tomography recording at the object itself or after data acquisition. In patent document DE 1020070081178 A1, by means of a pre-scan the proportion of scattered rays is determined depending on the angle and introduced into the computer tomography measurement. The proportion of scattered rays serves for calibrating the medical CT, so that the dose may be modulated depending on the angle, as for different x-ray directions through the patient different wavelengths results. In patent document U.S. Pat. No. 5,457,724 A a further pre-scan is described by means of which the position of the patient and its center are determined. In further methods by means of such a pre-scan the position of the patient is determined with the help of contrast agents. All of these methods which are based on a pre-scan need additional time and interaction of the operator with the CT.

SUMMARY

According to an embodiment, an image processing device of a computer tomography system may have an interface which is implemented to receive a first set of X-ray recordings of an object to be examined from first discrete recording angles and to receive a second set of X-ray recordings of the object to be examined from second discrete recording angles; and a calibration data determiner which is implemented to determine calibration data for the computer tomography system on the basis of the first set; wherein the first set is recorded during a first rotation run wherein the computer tomography system and the object to be examined rotate relative to each other and wherein the second set is recorded during at least a further rotation run after the first rotation run, wherein a computer tomography recording is reconstructable on the basis of the calibration data and on the basis of the first and second sets and wherein the first discrete recording angles differ from the second discrete recording angles.

According to another embodiment, a computer tomography system may have a recording unit which has a radiation source and a radiation detector associated with the radiation source and is implemented to record X-ray recordings of an object to be examined; an object carrier for the object to be examined; and an image processing device of a computer tomography system which may have an interface which is implemented to receive a first set of X-ray recordings of an object to be examined from first discrete recording angles and to receive a second set of X-ray recordings of the object to be examined from second discrete recording angles; and a calibration data determiner which is implemented to determine calibration data for the computer tomography system on the basis of the first set; wherein the first set is recorded during a first rotation run wherein the computer tomography system and the object to be examined rotate relative to each other and wherein the second set is recorded during at least a further rotation run after the first rotation run, wherein a computer tomography recording is reconstructable on the basis of the calibration data and on the basis of the first and second sets, wherein the first discrete recording angles differ from the second discrete recording angles.

According to another embodiment, a method for determining calibration data for a computer tomography system may have the steps of recording a first set of X-ray recordings of an object to be examined from first discrete recording angles during a first rotation run in which the computer tomography system and the object to be examined rotate relative to each other; determining calibration data for the computer tomography system on the basis of the first set; and recording a second set of X-ray recordings of the object to be examined from second discrete recording angles during the second rotation run, wherein a computer tomography recording is reconstructable on the basis of the calibration data and on the basis of the first and second sets and wherein the first discrete recording angles differ from the second discrete recording angles.

According to another embodiment, a computer program may have a program code for executing the method for determining calibration data for a computer tomography system which may have the steps of recording a first set of X-ray recordings of an object to be examined from first discrete recording angles during a first rotation run in which the computer tomography system and the object to be examined rotate relative to each other; determining calibration data for the computer tomography system on the basis of the first set; and recording a second set of X-ray recordings of the object to be examined from second discrete recording angles during the second rotation run, wherein a computer tomography recording is reconstructable on the basis of the calibration data and on the basis of the first and second sets, wherein the first discrete recording angles differ from the second discrete recording angles, when the program is executed on a computer.

Embodiments of the present invention provide an image processing device of a computer tomography system having an interface and a calibration data determiner. The interface is implemented to receive a first set of x-ray recordings of an object to be examined from first discrete recording angles and a second set of x-ray recordings of the object to be examined from second discrete recording angles. The calibration data determiner is implemented to determine calibration data for the computer tomography system on the basis of the first set. The first set is further recorded during a first rotation run wherein the computer tomography system and the object to be examined rotate relative to each other, wherein the second set is recorded during at least a further rotation run after the first rotation run. On the basis of the calibration data and the first and second sets a (two-dimensional or three-dimensional) computer tomography recording is reconstructable.

Embodiments of the present invention are based on the fact that calibration or correction data, like e.g. the relative position of the axis of rotation or other geometrical data may be determined directly during the measurement process. This calibration data is determined with respect to a first set of x-ray recordings of any object to be examined during a first rotation (e.g. by 360°). Here, the first (projection data) set advantageously comprising a reduced extent is determined within a short period of time in a first rotation run. When determining the calibration data on the basis of this reduced first set additional interactions of the system operator (e.g. exchange of the reference object with the object to be examined, shifting axes) is prevented and thus possible error sources are reduced. The extent of the first set is selected so that despite the reduced size reliable results for the calibration data may be expected on which the reconstruction of the computer tomography recording is based. In one or several further rotation runs now further x-ray recordings of the object may be recorded which belong to a second set (with a greater extent). On the basis of these additional x-ray recordings together with the calibration data and the already determined x-ray recordings of the first set, the reconstruction may be executed. As the reconstruction may already begin using the data of the first set before the second set has been recorded completely, the use of this image processing device or the method enables a substantial reduction of time in computer tomography.

According to further embodiments, the first discrete recording angles which serve for determining the calibration data are evenly distributed along a revolution or rotation of the first rotation run, wherein the second discrete recording angles are randomly distributed between the first discrete recording angles.

Further embodiments of the present invention provide a method for determining calibration data for a computer tomography system. The method comprises the step of recording a first set of x-ray recordings of an object to be examined from first discrete recording angles during a first rotation run in which the computer tomography system and the object to be recorded rotate relative to each other. Further, the method comprises the step of determining calibration data for the computer tomography system on the basis of the first set and the step of recording a second set of x-ray recordings of the object to be examined from second discrete recording angles during a second rotation run, wherein on the basis of the calibration data of the first and second sets a computer tomography recording is reconstructable. As the measurement is not influenced by an exchange of the reference object by the object to be examined, the accuracy and reproducibility of the results is improved. Artifacts in reconstruction are thus reduced which again has a positive effect on image quality and thus on readability of the computer tomography recording.

A further embodiment provides a computer tomography system comprising a recording unit, an object carrier and the above-described image processing device. The recording unit includes a radiation source and a radiation detector associated with the radiation source and is implemented to record x-ray recordings of the object to be examined. The recording unit and the object carrier are rotatable with respect to each other so that the first and second discrete recording angles may be approached. This may, for example, be realized by the object carrier being rotatable around an axis of rotation with respect to further embodiments. The advantage here is that for calibration no additional translational travel unit is needed so that manufacturing costs for the CT are reduced.

BRIEF DESCRIPTION OF THE DRAWINGS

Embodiments of the present invention will be detailed subsequently referring to the appended drawings, in which.

DETAILED DESCRIPTION OF THE INVENTION

Before embodiments are explained in more detail with reference to the figures in the following, it is noted that like or seemingly like elements are provided with the same reference numerals so that the description of the same may be mutually applied or exchanged.

Figure 1A:
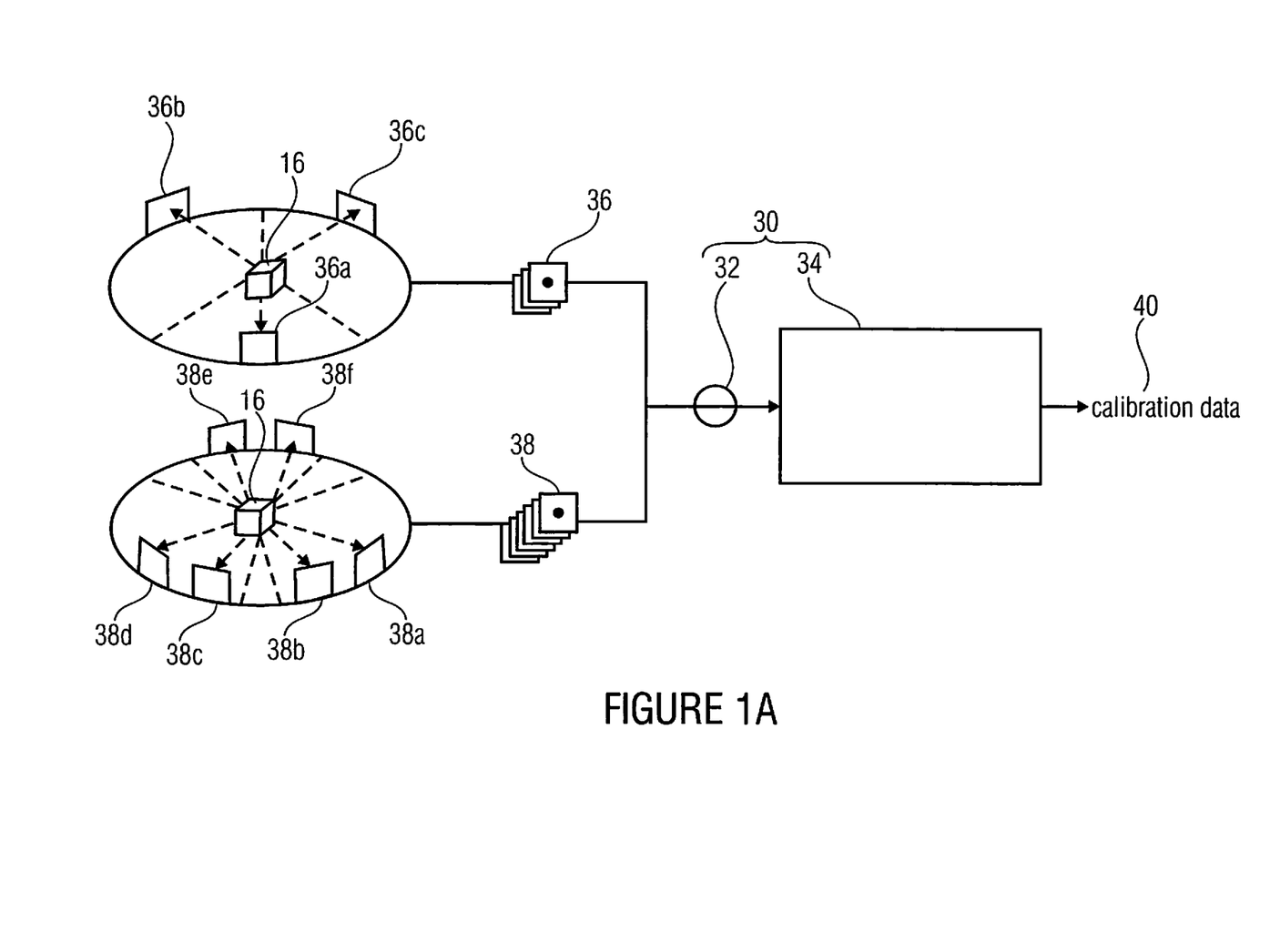
FIG. 1a is a schematical block diagram of an image processing device of a computer tomography system according to one embodiment.

FIG. 1a shows an image processing device 30 having an interface 32 and a calibration data determiner 34. The interface 32 is connected to a computer tomography system so that via the same a first set 36 of x-ray recordings of an object 16 to be examined, e.g. a human body or an industrially manufactured member, and a second set 38 of x-ray recordings of the same object 16 to be examined may be received.

The first set 36 of x-ray recordings is for example based on three x-ray recordings 36a, 36b and 36c, recorded during a first rotation run of the computer tomography system around the object 16 or the object 16 in the computer tomography system. By the rotation of the computer tomography system and the object 16 to be examined relative to each other the individual x-ray recordings 36a, 36b and 36c may be recorded from different discrete recording angles. On the basis of the first set 36, the calibration data determiner 34 determines the calibration data 40 and outputs the same for example to the computer tomography system or a computer tomography reconstructer. Calibration data may be different data, like e.g. geometrical data of the CT or a relative position of an axis of rotation or a tilting of the axis of rotation in the CT.

The determination of such calibration data is basically executed according to known methods or algorithm as they are for example described in patent document DE 4325351. In the embodiment according to FIG. 1a, however, no separate reference object is used for calibration, but the determination of the calibration data by means of the object 16 is executed. The relative position of the axis of rotation is for example detected on the basis of a shifting of the axis of rotation with respect to a reference point of the object 16 to be examined, e.g. the geometrical center, observed from different discrete recording angles. The geometrical center of the object 16 is determined in the attenuation profile as described in patent document U.S. Pat. No. 5,457,724. When plotting the position of the geometrical center with respect to the angular position along a complete rotation, the position of the center ideally travels along a sine function. The additive constant by which the course of the geometrical center deviates from a sine describes the distance of the center of rotation from the central beam 18 (see FIG. 3a). It is noted that his method for parallel beam geometry acquires a high computational accuracy while with cone beam geometry an approximation is used. The degree of deviation from a sinusoidal course additionally indicates a measure for the quality of calibration so that the data may be checked and evaluated immediately. In summary, this means that the determination of the relative position of the axis of rotation is executed analog to the proceedings using a reference object, wherein, however, a reference point of the object 16 to be examined itself forms the reference object. This offers the advantage that for the examination the object 16 does not have to be newly placed within the computer tomography system first, which means that no interference of the measurement takes place and all in all also the duration of a computer tomography process is shortened. For the determination of such calibration data 40 some few x-ray recordings 36a, 36b and 36c, like for example 40 or 36 x-ray recordings are sufficient so that the x-ray recordings 36a, 36b and 36c, for example every 10°, are recorded within the revolution or partial revolution and an additional pre-calibration (e.g. by means of a pre-scan) is not necessary.

On the basis of the determined calibration data and on the basis of the x-ray recordings 36a, 36b and 36c of the first set 36, in combination with x-ray recordings 38a, 38b, 38c, 38d, 38e and/or 38f of the second set 38, the computer tomography recording may be determined. In principle, the determination of the two-dimensional or three-dimensional computer tomography recording may already be started after the first set 36 has been received and evaluated completely, i.e. in particular before the second set 38 has been received completely, so that a fast but if applicable also incompletely resolved computer tomography recording may be represented. The background is here that the more different recording angles are used for the projected x-ray recordings, the greater the depth information is that may be reconstructed from the resulting set 38. Typically, the selected number of angles corresponds to the detector width in pixels×Pi/2. For a conventional three-dimensional computer tomography system with a detector which is, for example, 1024 pixels wide this means that approximately 1600 x-ray recordings are taken. It is advantageous here that both the x-ray recordings of the first set 36 and also the x-ray recordings of the second set 38 may be counted among the overall number of x-ray recordings so that the computer tomography recording may be output as fast as possible. It is noted here that advantageously the number of x-ray recordings of the first set 36 may be smaller by a factor of at least 2 or even at least 10 or 15 than the number of the x-ray recordings of the second set 38, as typically for the reconstruction of a computer tomography recording a higher information density is needed than for the calculation of the calibration data 40.

According to further embodiments, the image processing device comprises a computer tomography reconstructer which executes the reconstruction of a computer tomography recording and starts with the same after the first set 36 has been received and evaluated completely and in particular before the second set 38 has been received completely. According to a further alternative embodiment it is possible for the reconstruction of the computer tomography recording to be executed only after a complete recording of the second set 38 of the x-ray recordings.

Figure 1B:
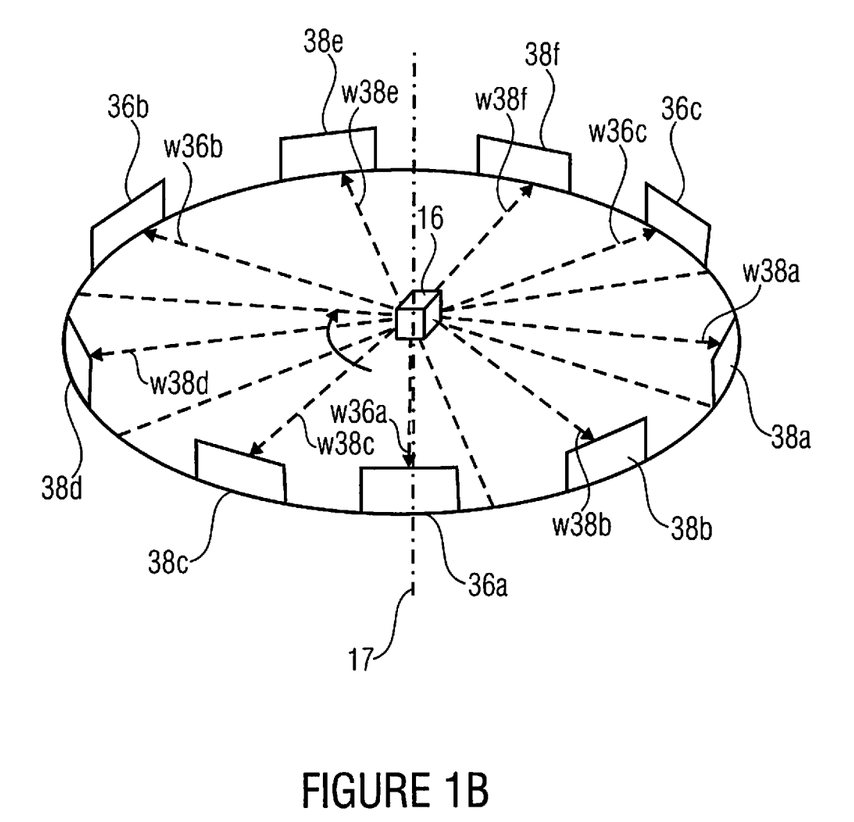
FIG. 1b is a schematical illustration of degrees of freedom of a computer tomography system for illustrating the different recording angles according to embodiments.

FIG. 1b shows a rotation circle of a recording unit of a computer tomography system around the object 16 in which the x-ray recordings 36a, 36b and 36c with the associated discrete recording angles w36a, w36b and w36c of the first set 36 and the x-ray recordings 38a, 38b, 38c, 38d, 38e and 38f with the associated discrete recording angles w38a, w38b, w38c, w38d, w38e and w38f of the second set 38 are illustrated. It is noted that the discrete recording angles w36a, w36b and w36c and w38a, w38b, 38c, 38d, 38e and 38f lie in one plane determined by the rotation circle. The discrete recording angles w36a, w36b and w36c are evenly distributed along the rotation circle, while two discrete recording angles each w38a and w38b, w38c and w38d as well as w38e and w38f are distributed between the discrete recording angles w36a, w36b and w36c.

The computer tomography system rotates around the rotation axis 17 during the first rotation run and the further rotation runs or approaches the discrete recording angles w36a, w36b and w36c, w38a, w38b, w38c, w38d, w38e and w38f of the first and second sets 36 and 38 in order to determine the x-ray recordings of the object 16. In this respect, the image processing device may according to further embodiments comprise a computer tomography controller which is implemented to control the computer tomography system. According to embodiments, the system is controlled so that in the first rotation run the recording angles w36a, w36b and w36c of the first set 36 are approached, while in a further rotation run after the completion of the first rotation run the discrete recording angles w38a, w38b, w38c, w38d, w38e and w38f of the second set 38 are approached.

According to further embodiments, the computer tomography system may be controlled so that more than one further rotation run is executed. Consequently, with a first further rotation run the recording of the discrete recording angles 38a, 38c and 38e is executed before in a second further rotation run the discrete recording angles 38b, 38c and 38f are approached. Insofar, this type of control offers the possibility to determine the complete second set 38 of the x-ray recordings by means of a plurality of rotations.

Figure 2A:
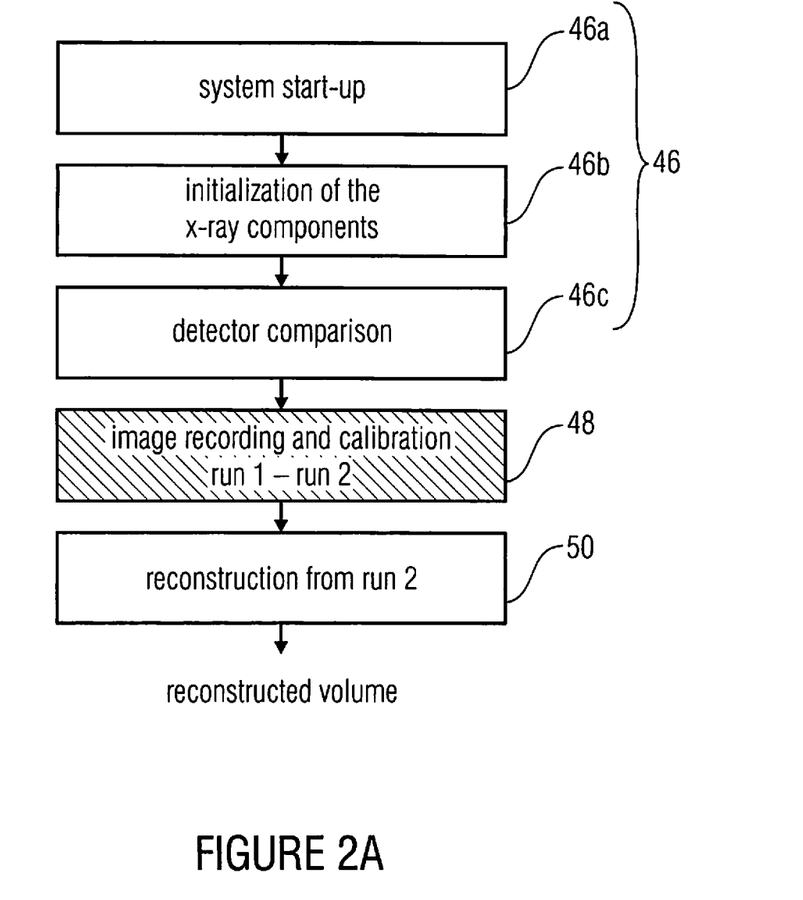
FIG. 2a-2b are schematical block diagrams for illustrating the method for calibration or for determining x-ray recordings according to embodiments.

FIG. 2a schematically illustrates the overall procedure with a computer tomography measurement with the reference-free calibration. The method is classified into three main steps. Initialization 46, image recording and calibration 48 and reconstruction 50.

In the initialization, the system start 46a, the initialization of the x-ray components 46b and the detector comparison 46c are executed. After executing this initialization 46, the computer tomography system is ready to record, so that an object may be placed within the same and the image recording and calibration 48 may be started. In principle, the image recording corresponds to the standard process, wherein however the sequence of the individual x-ray recordings is changed at the different recording angles. In contrast to the standard process, the individual x-ray recordings from the individual discrete recording angles (for example with 800 angles 0°, 0.45°, 0.9°, 1.35°, etc.) are not recorded in one single rotation but are determined with a changed order in several rotation runs. This process is illustrated in the details of the step of image recording and calibration 48 in FIG. 2b.

Figure 2B:
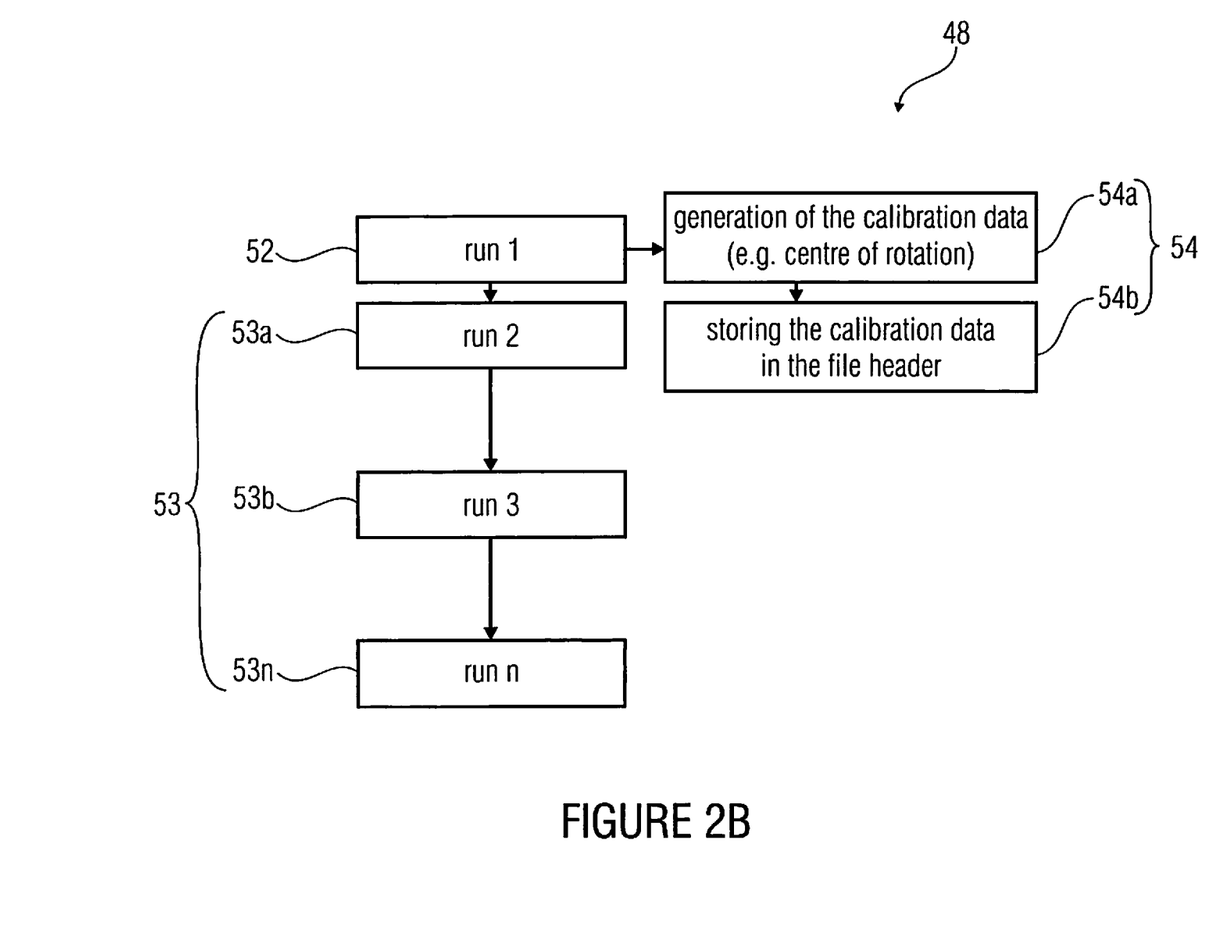

FIG. 2b shows the step of image recording and calibration 48 in detail without pre-scan, wherein this step includes the substeps of recording the first set 52 and recording the second set 53 which are executed in parallel to the step of determining the calibration data 54.

In the step of recording the first set 52, in a first rotation run for example the x-ray recordings are recorded with the recording angles of 0°, 20°, 40°, 60°, 80°, 100°, 120°, etc. in the mentioned or any other order. On the basis of this first set then the step of determining the calibration data 54 with the substeps of generating the calibration 54a and storing the calibration data 54b integrated in the measurement run, for example in the file header of the computer tomography recording is executed. After determining the first set 52 in a first rotation run or during the determination of the calibration data 54 the second set is determined 53, wherein in this respect for example n (e.g. 9) further rotation runs are executed. In the first further rotation run 53a the x-ray recordings with respect to the recording angles 1°, 21°, 41°, 61°, 81°, 101°, etc. are recorded in this or in any other order, while in a second further rotation run 53b the x-ray recordings with respect to the recording angles 2°, 22°, 42°, 62°, 82°, 102°, etc. are recorded. Using this process, in the n further rotation runs a plurality of x-ray recordings (e.g. 9×36 x-ray recordings) may be determined with respect to the x-ray recordings of the first set as supporting points for the reconstruction. It is noted that in principle the recording of the second set may be executed in any order, wherein advantageously the rotation direction is not changed during the recording of the second set 53, as the uni-directional approach accuracy is generally clearly higher than the bidirectional one.

On the basis of the determination of the x-ray recordings of the second set 53 the step of reconstruction 50 is executed (see FIG. 2a) which may in principle be executed after the step of determining the second set in a first further rotation run 53a and thus in parallel to the steps of determining the second set in a second further rotation run 53b. Here, the x-ray recordings made for the calculation of the calibration data are reused for the reconstruction in order to increase the database for the reconstruction.

The above described image processing device may either be used as a separate unit (e.g. in retrofitting) next to a CT, so that the calibration data determiner 34 (see FIG. 1a) is connected with the CT by the interface 32 and receives the first and second set 36 and 38 of x-ray recordings from the same, or may be part of the CT or an evaluation unit of the CT. Thus, a further embodiment of the invention provides a computer tomography system with the components described in FIG. 3a or 3b and the image processing device 30 according to FIG. 1a. Here, the image processing device 30 may be used both for CTs with a Gantry arrangement and also for CTs with a rotatable object carrier or a manipulation unit.

With respect to FIG. 1a, it is noted that the calibration data determiner 34 may also determine further calibration or correction data when determining the second set 38.

With respect to FIG. 1b it is noted that the proceedings when determining the second set 38 of the x-ray recordings may vary, so that for example after determining the first set, the second set is determined using a conventional scan. Alternatively, it would also be possible that in the determination of the second set, the rotation circle (projection space) is divided into segments (e.g. 0°-90°, 90°-180°, . . . ) which are scanned in a changed order. It would likewise be possible that in the determination of the second set random recording angles are approached. All of these scans have in common that when recording the first and second set the rotation does not uniformly rotate exactly once around the axis.

With respect to FIG. 2b, it is noted that the recording of the first set 52 does of necessarily have to be executed in one complete rotation so that for example after 350° the first set has been recorded completely and the computer tomography system (backwards) drives back to the position of 0° to start the recording of the second set 53. Such a partial rotation advantageously comprises a rotation space of at least 180° in addition to an opening angle of the image defined by the recording unit 10 or the width of the detector 14 and the distance of the detector 14 from the radiation source 12. In particular with CTs with a limited rotation space the recording of the first and second sets is done by such partial rotations.

With respect to FIG. 2b it is further noted that according to further embodiments the rotation space does not necessarily have to lie in one plane, but may also be implemented spirally. This is in particular the case with Helix or spiral CTs (see FIG. 3b). Thus, the described image processing device 30 or the described method may also be used with Helix CTs which may for example comprise a tilted axis of rotation 17 as long as the tilting of the axis of rotation 17 is known and advantageously remains constant during the measurement.

It is further noted that the step of generating the calibration data 54a may advantageously be executed iteratively, so that the calibration data is determined in more detail on the basis of additional x-ray recordings of the first and/or second set. This iterative method is for example also used in the conversion of the central detector line on parallel beam geometry (in case of computer tomography systems with flat screen detectors or with only one detector line). In case of a flat screen detector the evaluation of the middle detector line is sufficient. Since different recording angles at defined object structures lead to geometrical distortions, the determined image information is first of all converted to parallel beam geometry in which respect the exact position of the center of rotation or the axis of rotation is used. As exactly this position is to be determined, however, the above-noted iterative method is used which alternatingly calculates the parallel beam geometry using an estimated initial value for the position of the axis of rotation and using the same then again calculates the position of the center of rotation. It was thus possible to show that this iterative method, even with an offset of the rotary center by 50 pixels, converges already after a few iterations.

According to a further embodiment, the number of x-ray recordings 36a, 36b, or 36c of the first set 36 is approximately of the same size (with a tolerance of +/−20%) or even greater (e.g. double as large as) than the number of x-ray recordings 38a, 38b, 38c, 38d, 38e and/or 38f of the second set 38 which offers the advantage that the calibration data may thus be determined very precisely.

Although some aspects were described in connection with an image processing device, it is obvious that these objects also represent a description of the corresponding method for the determination of calibration data for a computer tomography system, so that a block or a member of a device may also be regarded as a corresponding method step or as a feature of a method step. Analog to that, aspects which were described in connection with or as a method step also represent a description of the corresponding block or detail or feature of a corresponding device. Some or all method steps may be executed by a hardware apparatus (or using a hardware apparatus) like e.g. a microprocessor, a programmable computer or an electronic circuit. In some embodiments, some or more of the important method steps may be executed by such an apparatus.

Depending on the respective implementation effort, embodiments of the invention may be implemented in hardware or in software, like e.g. in the Volex software. The implementation may be executed using a digital storage medium, for example a Blue-ray disc, a CD, an ROM, a PROM, an EPROM, an EEPROM or a FLASH memory, a hard disc or any other magnetical or optical memory on which electronically readable control signals are stored which may cooperate or do cooperate with a programmable computer system such that the respective method is executed. Thus, the digital storage medium may be computer readable.

Some embodiments according to the invention thus include a data carrier comprising electronically readable control signals which are able to cooperate with a programmable computer system such that one of the methods described herein is executed.

In general, embodiments of the present invention may be implemented as a computer program product having a program code, wherein the program code is effective to execute one of the methods when the computer program product runs on a computer. The program code may for example also be stored on a machine-readable carrier. Other embodiments include the computer program for executing one of the methods described herein, wherein the computer program is stored on a machine-readable carrier.

In other words, an embodiment of the inventive method is thus a computer program comprising a program code for executing one of the methods described herein, when the computer program is executed on a computer.

A further embodiment of the inventive method is thus a data carrier (or a digital storage medium or a computer-readable medium) on which the computer program for executing one of the methods described herein is recorded. A further embodiment of the inventive method thus is a data stream or a sequence of signals representing the computer program for executing one of the methods described herein. The data stream or the sequence of signals may, for example, be configured to be transferred via a data communication connection, for example via the interne.

A further embodiment includes a processing means, for example a computer or a programmable logics device configured or adapted in order to execute one of the methods described herein. A further embodiment includes a computer on which the computer program for executing one of the methods described herein is installed.

A further embodiment according to the invention includes a device or a system implemented to transfer a computer program for executing at least one of the methods described herein to a receiver. The transfer may for example be executed electronically or optically. The receiver may for example be a computer, a mobile device, a memory device or a similar device. The device or the system may for example include a file server for transferring the computer program to the receiver.

In some embodiments, a programmable logics device (for example a field-programmable gate array, an FPGA) may be used to execute some or all functionalities of the methods described herein. In some embodiments a field programmable gate array may cooperate with a microprocessor to execute one of the methods described herein. In general, in some embodiments the methods are executed by any hardware device. The same may be universally usable hardware like a computer processor (CPU) or hardware which is specific for the method, like, for example, an ASIC.

The above-described embodiments merely represent an illustration of the principles of the present invention. It is obvious that modifications and variations of the arrangements and details described herein are obvious to other persons skilled in the art. It is thus the object for the invention to be merely limited by the scope of the following patent claims and not by the specific details presented herein with respect to the description and the explanation of the embodiments.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An image processing device of a computer tomography system, comprising:
an interface which is implemented to receive a first set of X-ray recordings of an object to be examined from first discrete recording angles and to receive a second set of X-ray recordings of the object to be examined from second discrete recording angles; and
a calibration data determiner which is implemented to determine calibration data for the computer tomography system on the basis of the first set;
wherein the first set is recorded during a first rotation run wherein the computer tomography system and the object to be examined rotate relative to each other and wherein the second set is recorded during at least a further rotation run after the first rotation run,
wherein a computer tomography recording is reconstructable on the basis of the calibration data and on the basis of the first and second sets,
wherein the first discrete recording angles differ from the second discrete recording angles.

2. The image processing device according to claim 1, wherein the calibration data comprise geometrical data of the computer tomography system.

3. The image processing device according to claim 2, wherein the geometrical data comprises at least either a relative position of an axis of rotation in the computer tomography system around which the computer tomography system or the object to be examined rotate or a tilting of the axis of rotation with respect to an X-ray direction of the computer tomography system.

4. The image processing device according to claim 3, wherein the calibration data determiner is implemented to determine the relative position of the axis of rotation by the detection of a shifting of a reference point of the object to be examined in the X-ray recordings of the first set.

5. The image processing device according to claim 1, comprising a computer tomography controller which is implemented to control the computer tomography system in order to approach the first and second discrete recording angles.

6. The image processing device according to claim 1, wherein the first discrete recording angles are distributed randomly along one revolution of the first rotation run.

7. The image processing device according to claim 1, wherein the first discrete recording angles are distributed evenly along a revolution of the first rotation run.

8. The image processing device according to claim 1, wherein the first rotation run and/or the second rotation run comprise partial rotations.

9. The image processing device according to claim 1, wherein the second discrete recording angles are distributed along one revolution or partial rotation of the at least one further rotation run and are randomly distributed between the first discrete recording angles.

10. The image processing device according to claim 9, wherein the second discrete recording angles are distributed evenly between the first discrete recording angles.

11. The image processing device according to claim 1, wherein between 2 and 20 discrete recording angles of the second set are distributed between the first discrete recording angles.

12. The image processing device according to claim 1, wherein the second set is recorded during a plurality of further rotation runs.

13. The image processing device according to claim 1, comprising a computer tomography reconstructor which is implemented to reconstruct the computer tomography recording on the basis of the calibration data and the first and second sets and to start the reconstruction after the first set has been received and evaluated completely and in particular before the second set has been received completely.

14. The image processing device according to claim 1, wherein the first set comprises a smaller number of discrete recording angles than the second set.

15. The image processing device according to claim 1, wherein the number of X-ray recordings of the first set is smaller by a factor of at least 2 than the number of X-ray recordings of the second set.

16. The image processing device according to claim 1, wherein the number of X-ray recordings of the first set is smaller by a factor of a maximum of 0.2 than the number of X-ray recordings of the second set or wherein the number of X-ray recordings of the first set corresponds to the number of X-ray recordings of the second set.

17. The image processing device according to claim 1, wherein the number of X-ray recordings of the first set is greater than the number of X-ray recordings the second set.

18. The image processing device according to claim 1, wherein the object recorded by the first set of x-ray recordings is identical to the object recorded by the second set of x-ray recordings.

19. The image processing device according to claim 1, wherein the second set of x-ray recordings enables to increase a depth information for reconstructing the computer tomography recording of the object.

20. A computer tomography system, comprising:
a recording unit which comprises a radiation source and a radiation detector associated with the radiation source and is implemented to record X-ray recordings of an object to be examined;
an object carrier for the object to be examined; and
an image processing device of a computer tomography system, comprising:
an interface which is implemented to receive a first set of X-ray recordings of an object to be examined from first discrete recording angles and to receive a second set of X-ray recordings of the object to be examined from second discrete recording angles; and
a calibration data determiner which is implemented to determine calibration data for the computer tomography system on the basis of the first set;
wherein the first set is recorded during a first rotation run wherein the computer tomography system and the object to be examined rotate relative to each other and wherein the second set is recorded during at least a further rotation run after the first rotation run,
wherein a computer tomography recording is reconstructable on the basis of the calibration data and on the basis of the first and second sets, wherein the first discrete recording angles differ from the second discrete recording angles;
wherein the recording unit and the object carrier are rotatable relative to each other in order to approach the first and second discrete recording angles.

21. The computer tomography system according to claim 20, wherein the object carrier is rotatable around an axis of rotation which is tilted with respect to an X-ray direction extending along the recording unit.

22. The computer tomography system according to claim 20, wherein the recording unit is rotatable around an axis of rotation and around the object.

23. A method for determining calibration data for a computer tomography system, comprising:
recording a first set of X-ray recordings of an object to be examined from first discrete recording angles during a first rotation run in which the computer tomography system and the object to be examined rotate relative to each other;
determining calibration data for the computer tomography system on the basis of the first set; and
recording a second set of X-ray recordings of the object to be examined from second discrete recording angles during the second rotation run,
wherein a computer tomography recording is reconstructable on the basis of the calibration data and on the basis of the first and second sets,
wherein the first discrete recording angles differ from the second discrete recording angles.

24. The method according to claim 23 comprising a further step of reconstructing the computer tomography recording at the same time of recording the second set, wherein the reconstruction begins after the first set has been received and evaluated completely and in particular before the second set has been received completely.

25. A non-transitory computer-readable medium encoded with a computer program comprising a program code for executing the method for determining calibration data for a computer tomography system, comprising:
recording a first set of X-ray recordings of an object to be examined from first discrete recording angles during a first rotation run in which the computer tomography system and the object to be examined rotate relative to each other;
determining calibration data for the computer tomography system on the basis of the first set; and
recording a second set of X-ray recordings of the object to be examined from second discrete recording angles during the second rotation run,
wherein a computer tomography recording is reconstructable on the basis of the calibration data and on the basis of the first and second sets, wherein the first discrete recording angles differ from the second discrete recording angles, when the program is executed on a computer.

* * * * *